United States Patent [19]

Herzog et al.

[11] Patent Number: 5,011,809
[45] Date of Patent: Apr. 30, 1991

[54] PREPARATION OF A SILVER CATALYST

[75] Inventors: Klaus Herzog, Ludwigshafen; Karl-Heinz Boehning, Darmstadt; Heinrich Aichinger, Mannheim; Juergen Plueckhan; Wolf D. Mross, both of Frankenthal; Matthias Schwarzmann, Limburgerhof, all of Fed. Rep. of Germany

[73] Assignee: BASF Aktiengesellschaft, Ludwigshafen, Fed. Rep. of Germany

[21] Appl. No.: 471,544

[22] Filed: Jan. 29, 1990

[30] Foreign Application Priority Data

Feb. 23, 1989 [DE] Fed. Rep. of Germany ....... 3905578

[51] Int. Cl.$^5$ .................. B01J 21/04; B01J 23/04; B01J 23/50
[52] U.S. Cl. ..................... 502/348; 502/25; 502/26; 502/347
[58] Field of Search .................... 502/25, 26, 347, 348

[56] References Cited

U.S. PATENT DOCUMENTS

| 4,123,385 | 10/1978 | Rebsdat et al. | 252/414 |
| 4,324,699 | 4/1982 | Mross et al. | 252/463 |
| 4,335,014 | 6/1982 | Alfranseder et al. | 252/412 |
| 4,471,071 | 9/1984 | Rebsdat et al. | 502/347 |
| 4,740,493 | 4/1988 | Boehning et al. | 502/348 |
| 4,829,043 | 5/1989 | Boehning et al. | 502/348 |

FOREIGN PATENT DOCUMENTS

| 573867 | 6/1988 | Australia . |
| 0099975 | 2/1984 | European Pat. Off. . |
| 0211397 | 2/1987 | European Pat. Off. . |
| 1413251 | 11/1975 | United Kingdom . |
| 1601635 | 11/1981 | United Kingdom . |

*Primary Examiner*—W. J. Shine
*Attorney, Agent, or Firm*—John H. Shurtleff

[57] ABSTRACT

Supported silver catalysts which contain one or more alkali metals are prepared in a two-stage process by doping a basic catalyst which contains silver in metallic form and may also contain lithium with the heavy alkali metal sodium, potassium, rubidium and/or cesium using an impregnating solution which contains the heavy alkali metal and one or more nitrates of the general formula $$R^+NO_3^-$$

wherein $R^+$ is an ammonium, hydrazinium, $C_1$-$C_{12}$-monoalkylammonium, $C_2$-$C_{12}$-dialkylammonium, $C_3$-$C_{12}$-trialkylammonium or $C_4$-$C_{12}$-tetraalkylammonium cation.

5 Claims, No Drawings

PREPARATION OF A SILVER CATALYST

The present invention relates to a two-stage process for preparing a supported catalyst which contains silver and an alkali metal by doping a basic catalyst which contains silver in metallic form and may also contain lithium with the heavy alkali metal sodium, potassium, rubidium and/or cesium.

The present invention also relates to a process for preparing ethylene oxide.

Catalysts for preparing ethylene oxide which besides metallic silver contain the heavy alkali metals sodium, potassium, rubidium and/or cesium with or without the light alkali metal lithium are known for example from DE-A-2 300 512 and DE-A-2 819 595. Although the technology of preparing these catalysts may be considered relatively mature, the fact that ethylene oxide is produced in large amounts means there is a constant demand for improved production methods whereby the properties of these catalysts, such as selectivity, activity and lifetime, can be improved still further. Accordingly, there is a great deal of interest in the development of better methods for preparing such silver catalysts, most of the prior art being concerned with the optimal application of the individual catalyst components to the carrier.

However, there is no general agreement about the best way of applying the silver and the alkali metals to the carrier (in general α-alumina), whether together or separately, and if separately, in which order, or about the use of impregnating aids, such as complexing agents, surfactants, reducing agents etc. (cf. EP-B-14 457). In fact, the prior art reveals widely differing views on these matters.

For instance, DE-A-2 300 512 says that the simultaneous, "single-stage" application of the silver and of the alkali metal promoters is particularly advantageous. EP-A-168 782 discloses that the effectiveness of ethylene oxide production silver catalysts whose selectivity has decreased with increasing time-on-stream can be improved by doping them with a heavy alkali metal cation such as rubidium or in particular cesium.

Said European Patent Application also teaches that catalysts prepared in a "single-stage" or in a "two-stage" process (stage 1: application of silver; stage 2: application of the alkali metal promoters) are equivalent to one another when the subsequent application of the heavy alkali metal promoters takes place on a thermally stabilized, unused silver catalyst. Yet, according to DE-A-2 819 595, it is possible to prepare a catalyst in two stages (stage 1: application of silver and lithium; stage 2: application of the heavy alkali metal promoters) which for the same selectivity is more active than a single-stage catalyst by applying the heavy alkali metal promoters in stage 2 to an Ag- and Li-containing basic catalyst in the presence of a surface-active substance.

It is an object of the present invention to provide an improved process for preparing, in particular doping, more effective heavy alkali metal promoter/silver catalysts for the production of ethylene oxide.

We have found that this object is achieved by a two-stage process for preparing a supported catalyst which contains silver and an alkali metal by doping a basic catalyst which contains silver in metallic form and may also contain lithium with the heavy alkali metal sodium, potassium, rubidium or cesium using an impregnating solution which contains the heavy alkali metal and one or more nitrates of the general formula $$R^+NO_3^-$$

where $R^+$ is an ammonium, hydrazinium, $C_1$–$C_{12}$-monoalkylammonium, $C_2$–$C_{12}$-dialkylammonium, $C_3$–$C_{12}$-trialkylammonium or $C_4$–$C_{12}$-tetraalkylammonium cation.

We have also found a process for preparing ethylene oxide using a catalyst prepared as described above.

The process according to the present invention thus is actually only concerned with stage 2 of the preparation of two-stage supported silver catalysts doped with heavy alkali metal cations.

The measures of stage 1, i.e. the application to the carrier of the silver with or without lithium and subsequent heat treatment, viz. the preparation of the basic catalyst, do not form part of the subject-matter of the present invention. As regards the preparation of the basic catalyst, therefore, reference is made to the prior art, for example to GB-B-1 601 635, US-A-4 829 043 and AU-B-573 867.

According to the present invention, the impregnating solution which contains a heavy alkali metal cation for use as promoter has added to it one or more nitrates of the formula $$R^+NO_3^-$$

where $R^+$ is ammonium, hydrazinium or alkylammonium, such as $C_1$–$C_{12}$-monoalkylammonium, $C_2$–$C_{12}$-dialkylammonium, $C_3$–$C_{12}$-trialkylammonium or $C_4$–$C_{12}$-tetraalkylammonium, preferred ammonium $R^+$ containing not more than 8, in particular not more than 4, carbon atoms in the alkyl moiety. Unsubstituted ammonium and hydrazinium nitrates and hydrazinium dinitrates are particularly effective and hence particularly preferred.

The alkylammonium cations do of course also include ammonium cations of alkylenediamines, -triamines and -tetraamines, which have the same effect as the alkylammonium cations mentioned. The nature of the alkyl groups in the alkylammonium cations is not critical; that is, said cations may contain not only unbranched or branched alkyl groups but also cycloalkyl groups. It is of course also possible to use mixtures of various nitrates $R^+NO_3^-$ in the process according to the present invention without thereby impairing its success.

The ammonium, hydrazinium and alkylammonium nitrates in question, hereinafter referred to as nitrates for short, are applied to the basic silver catalyst which may contain lithium in an impregnating solution. This impregnating solution, besides the nitrates and a water-soluble organic solvent, contains water and the alkali metal promoter(s) to be applied.

Suitable water-soluble organic solvents are in particular water-soluble amines such as sec-butylamine, tert-butylamine, propylamine and isopropylamine, but good results were also obtained with alcohols, such as methanol, ethanol and isopropanol. It is also possible to use other polar, water-soluble organic solvents, for example formamides and alkylformamides.

The alkali metal promoter is advantageously added to the impregnating solution in the form of an aqueous solution, the water content of the impregnating solution preventing precipitation of the alkali metal salt. The anion of the alkali metal salt is basically freely choosable; however, it is particularly advantageous to use the alkali metal nitrates.

The precise effect of the nitrates in the impregnation of the catalyst with alkali metal cations is not as yet fully understood, but their advantageous effect on the properties of the silver catalysts thus prepared is evidently more due to the nitrate anion than to the ammonium cation. This is supported by the observation that increasing the number of carbon atoms in the ammonium cation, i.e. increasing the proportion of the molecular weight of the ammonium nitrate accounted for by the ammonium cation, has the effect of reducing the effectiveness of ammonium nitrates correspondingly and that it is necessary to make good the decreased effectiveness by increasing the amount of alkylammonium nitrate added.

In general, the basic catalyst has applied to it, based on the basic catalyst, from 1 to 30, preferably from 3 to 25, particularly advantageously from 5 to 15, % by weight of ammonium nitrate ($NH_4NO_3$). The amount of alkylammonium nitrate added is in general higher in proportion to its lower nitrate content compared with ammonium nitrate. Since the effectivenesses of the nitrates $R^+NO_3^-$ and the nitrate contents in the particular $R^+NO_3^-$ molecules are not directly proportional to each other, it is advisable, if alkylammonium nitrates are to be used, first to carry out a laboratory trial to determine the best amount of the particular alkylammonium nitrate which should be used.

Advantageously, the impregnating solution is employed in a relatively concentrated form, with the proviso that its concentration is such that, on the one hand, nitrates and alkali metal promoters stay in solution and do not precipitate and, on the other, that the volume of this solution remain sufficiently small that, on mixing with a certain amount of the basic catalyst to be impregnated, the solution is completely absorbed by said catalyst. The total volume and the composition of the impregnating solution composed of the components: organic solvent, water, nitrate and alkali metal promoter, or alkali metal promoter solution, can vary within those wide limits. The possible maximum and minimum quantities within those wide limits of each of these individual components of the 4-component mixture depends on the nature and amount of the other components used and of course also on the sorption properties of the basic catalyst, so that it is not possible to specify a general rule whereby the concentrations of the particular individual components used can be related. In general, suitable mixing ratios are easily determinable by a few mixing tests in a test tube.

In general, the alkali metal promoters are applied to the basic catalyst with the aid of such an impregnating solution in such a way that, as mentioned above, said basic catalyst completely absorbs the impregnating solution. It can prove advantageous here if the mixture thus obtained is left to stand for some time for the purpose of equilibration. An advantageous equilibration time is from 0.5 to 6 hours. Thereafter, the catalyst is heat-treated, advantageously in a stream of nitrogen, at from 180 to 300° C., advantageously from 200 to 250° C., in particular from 220 to 250° C. At these temperatures the added nitrate generally decomposes—and possibly develops its effect—within a few minutes. The catalyst thus obtained can be used directly for preparing ethylene oxide.

Catalysts having particularly favorable properties are obtained by the present doping method if the heavy alkali metals sodium, potassium, rubidium and/or cesium are deposited on the basic catalyst in amounts of from 0.0005 to 0.06% by weight, based on the total catalyst.

The present method of impregnation has a particularly advantageous effect on the performance of those silver catalysts which have silver contents of from 2 to 18% by weight and lithium contents of from 0.0005 to 0.3% by weight, both percentages being based on the total catalyst.

A suitable carrier material for the present process for preparing a silver catalyst is α-alumina, in particular α-alumina having a purity of more than 99%, a BET surface area of 0.4 m$^2$/g to 0.8 m$^2$/g and a pore volume of not less than 0.4 cm$^3$/g.

Ethylene oxide can be produced using the silver catalysts according to the present invention in a conventional manner as represented for example in the prior art references cited. The silver catalysts obtainable by the process according to the present invention are surprisingly notable for high activity, high selectivity and a long life.

EXAMPLES

The experiments described were carried out using an α-alumina carrier material which met the requirements listed in Table 1.

TABLE 1

| Carrier material requirements | |
|---|---|
| Purity of α-Al$_2$O$_3$ | about 99% by wt. |
| Level of SiO$_2$ | about 0.1–0.5% by wt. |
| Soluble ions | |
| Al | 250–2000 ppm by wt. |
| Ca | 150–2000 ppm by wt. |
| K | 20–1000 ppm by wt. |
| Na | 50–1000 ppm by wt. |
| BET surface area | 0.4–0.8 m$^2$/g |
| Water uptake | |
| cold (20° C.) | 0.4–0.5 cm$^3$/g |
| hot (100° C.) | 0.45–0.55 cm$^3$/g |
| Bulk density | 600–800 kg/m$^3$ |

Preparation of the basic catalyst:

The basic catalyst was prepared by the method of EP-A-271 814.

100 g of the α-alumina carrier were impregnated with a solution of 24.2 g of sec.-butylamine, 5.9 g of water, 27.3 g of silver nitrate and 160 mg of lithium nitrate, the mixture was left at room temperature for 3 hours and then transferred into a through-circulation oven where it was heat-treated at 240° C. in nitrogen. The basic catalyst thus obtained contained 14% by weight of silver and 130 ppm by weight of lithium.

EXAMPLE 1

100 g of basic catalyst were admixed in a mixer with a solution containing 17.4 g sec.-butylamine, 4.7 g of water, 13.9 g of ammonium nitrate and 0.48 ml of a cesium nitrate solution having a cesium content of 68.2 g/l. After the impregnating liquid had been completely absorbed by the basic catalyst, the catalyst precursor thus obtained was left at room temperature for 3 hours and then heat-treated in a through-circulation oven at 230° C. in nitrogen for 20 minutes. The catalyst thus prepared (hereinafter referred to as A) contained 300 ppm by weight of cesium as well as the ingredients of the basic catalyst.

EXAMPLE 2

The catalyst was prepared as described in Example 1, except that the impregnating solution contained only 10.6 g of ammonium nitrate (hereinafter this catalyst will be referred to as B).

EXAMPLE 3 (COMPARATIVE EXAMPLE)

The catalyst was prepared as described in Example 1, except that the impregnating solution contained no ammonium nitrate (hereinafter this catalyst will be referred to as C).

Preparation of ethylene oxide

The catalysts prepared in Examples 1 to 3 were comminuted and classified. 10 g of each of the fractions 0.6-0.75 mm were introduced into a thermostatable stainless steel reactor 5 mm in internal diameter. A gas mixture of 30% of ethylene, 8% of oxygen, 4% of carbon dioxide and 5 ppm of vinyl chloride (inhibitor), the remainder being nitrogen, was passed through the reactor. The pressure was adjusted to 16 bar. The space velocity over the catalyst was 3300 standard l of gas/l of catalyst. The temperature was controlled in such a way that the oxygen conversion was 30%. Samples were taken after a run of 3 days to determine the activity and selectivity of the catalyst. The data found are given in Table 2.

TABLE 2

| Catalyst | Activity T (°C.) | Selectivity S (%) |
| --- | --- | --- |
| A | 220 | 82.5 |
| B | 217 | 82.8 |
| C | 216 | 81.7 |

We claim:

1. In a two-stage process for preparing a carrier supported catalyst which contains silver and an alkali metal wherein the initial carrier supported catalyst is prepared in a first stage to contain metallic silver and may also contain the light alkali metal lithium, and this initial catalyst is then doped in a second stage with an impregnating solution containing a heavy alkali metal cation selected from the group consisting of sodium, potassium, rubidium and cesium, the improvement which comprises:

using in said second stage an impregnating solution which contains said heavy alkali metal and one or more nitrates of the formula $$R^+NO_3^-$$

where $R^+$ is an ammonium, hydrazinium, $C_1$–$C_{12}$-monoalkylammonium, $C_2$–$C_{12}$-dialkylammonium, $C_3$–$C_{12}$-trialkylammonium or $C_4$–$C_{12}$-tetraalkylammonium cation.

2. A process as claimed in claim 1, wherein the initial catalyst used contains 2-18% by weight of silver and 0.0005-0.3% by weight of lithium.

3. A process as claimed in claim 1, wherein the impregnating solution deposits from 0.0005 to 0.06% by weight of sodium, potassium, rubidium and/or cesium on the initial carrier supported catalyst.

4. A process as claimed in claim 1, wherein the carrier material used is more than 99% by weight high-purity α-alumina and has a BET surface area of 0.4-0.8 m$^2$/g and a pore volume of not less than 0.4 cm$^3$/g.

5. A process as claimed in claim 1, wherein the compound $R^+NO_3^-$ is ammonium nitrate employed in an amount of from 1 to 30% by weight, based on the initial catalyst.

* * * * *